(12) United States Patent
Lyndin et al.

(10) Patent No.: US 6,218,194 B1
(45) Date of Patent: Apr. 17, 2001

(54) ANALYTICAL METHODS AND APPARATUS EMPLOYING AN OPTICAL SENSOR DEVICE WITH REFRACTIVE INDEX MODULATION

(75) Inventors: Nikolai Mikhailovich Lyndin; Vladimir Alexandrovich Sychugov; Alexander Valentinovich Tishchenko; Boris Alexandrovich Usievich, all of Moscow (RU)

(73) Assignee: Thermo Fast UK Limited (GB)

( * ) Notice: Subject to any disclaimer, the term of this patent is extended or adjusted under 35 U.S.C. 154(b) by 0 days.

(21) Appl. No.: 09/117,761

(22) PCT Filed: Feb. 10, 1997

(86) PCT No.: PCT/GB97/00346

§ 371 Date: Oct. 12, 1999

§ 102(e) Date: Oct. 12, 1999

(87) PCT Pub. No.: WO97/29362

PCT Pub. Date: Aug. 14, 1997

(30) Foreign Application Priority Data

Feb. 8, 1996 (GB) .................................... 9602542

(51) Int. Cl.[7] ................................................ G01N 33/543
(52) U.S. Cl. ........................ 436/518; 436/527; 436/164; 436/805; 356/128; 356/136; 356/328; 359/566; 359/569; 359/573; 359/885; 359/888; 359/637; 359/640; 359/890; 359/896; 359/572; 385/10; 385/12; 385/30; 385/36; 385/37; 385/129; 422/82.05; 422/82.09; 422/82.11
(58) Field of Search ..................................... 436/164, 805, 436/518, 527; 356/128, 136, 328; 359/566, 569, 573, 574, 885, 888, 637, 640, 890, 896, 572; 385/10, 12, 30, 36, 37, 129; 422/82.05, 82.09, 82.11

(56) References Cited

U.S. PATENT DOCUMENTS

| | | | |
|---|---|---|---|
| 4,521,522 | * | 6/1985 | Lundstrom et al. . |
| 4,558,012 | * | 12/1985 | Nygren et al. . |
| 5,017,009 | * | 5/1991 | Schutt et al. . |
| 5,071,248 | * | 12/1991 | Tiefenthaler et al. . |
| 5,313,264 | * | 5/1994 | Ivarsson et al. . |
| 5,327,225 | * | 7/1994 | Bender et al. . |
| 5,341,215 | * | 8/1994 | Seher . |
| 5,455,178 | * | 10/1995 | Fattinger . |
| 5,485,277 | * | 1/1996 | Foster . |
| 5,573,956 | * | 11/1996 | Hanning . |
| 5,641,640 | * | 6/1997 | Hanning . |
| 5,822,472 | * | 10/1998 | Danielzik et al. . |
| 5,832,165 | * | 11/1998 | Reichert et al. . |
| 6,127,183 | * | 10/2000 | Ivarsson et al. ........................ 436/34 |

FOREIGN PATENT DOCUMENTS

WO 97/09618 * 3/1997 (WO) .

OTHER PUBLICATIONS

Tamir et al. (1977). Analysis and design of grating couplers. Appl. Phys. 14:235–254.*

Fattinger et al. (1995). bidiffractive grating coupler: universal transducer for optical interface analytics. Opt. Eng. 34(9):2744–2753.*

* cited by examiner

Primary Examiner—Christopher L. Chin
Assistant Examiner—Minh-Quan K. Pham
(74) Attorney, Agent, or Firm—Nixon Peabody LLP

(57) ABSTRACT

A method for monitoring the interaction of molecular species utilizes a sensor device comprising a substrate (1) with a waveguide (2) formed on the surface thereof. A grating (3) is formed in one of the surfaces of the waveguide (2). A beam of light (6) is incident on the grating (3) and the angle of incidence at which maximum reflection occurs is monitored. A first molecular species is immobilized on the waveguide (2). Changes in the angular position of the reflection maximum provide an indication of interaction of the first molecular species with a second molecular species contained in a sample brought into contact with the sensor device.

43 Claims, 4 Drawing Sheets

ANALYTICAL METHODS AND APPARATUS EMPLOYING AN OPTICAL SENSOR DEVICE WITH REFRACTIVE INDEX MODULATION

CROSS-REFERENCE TO RELATED APPLICATIONS

This Application is a national stage application of PCT application No. PCT/GB97/00346, filed Feb. 10, 1997, which claims priority of Great Britain Application No. 9602542.4, filed Feb. 8,1996.

FIELD OF THE INVENTION

This invention relates to methods and apparatus for the analysis of analyte molecular species in a sample.

BACKGROUND OF THE INVENTION

Devices are known with a surface on which is immobilized a layer of biomolecules having an affinity for other molecules ("the analyte") in a sample under test. Such devices are commonly referred to as biosensors. The immobilized biomolecules and the analyte may, for example, constitute a specific binding pair such as an antigen-antibody pair. Interaction of the two members of the pair causes a change in the physical properties of the device. This change can be used as an indicator of the presence and/or concentration of the analyte, the strength and/or progress of the interaction etc.

In many biosensors, it is the optical properties of the device which are monitored. One class of optical biosensor comprises a waveguide in the form of a thin layer of relatively high refractive index material coated on a substrate of optically transparent lower refractive index material. Biomolecules are immobilized on the surface of the waveguide and the interface between the substrate and the waveguide is irradiated with a beam of light.

Means are generally provided to facilitate coupling of light into the waveguide. The optical properties of the device will depend on the nature of those means, as well as on other factors including the wavelength of the incident light, the materials used for the waveguide and the substrate, the thickness of the waveguide etc. In general, however incident light is coupled to a greater or lesser extent into the waveguide. Chemical binding events at or in the vicinity of the waveguide surface will cause a localized change in refractive index, which in turn causes a change in the coupling characteristics of the device. This provides a means for monitoring interactions between the immobilized biomolecules and the analyte molecules.

One form of coupling means which has been proposed is a grating structure formed, for instance, in the interface between the substrate and the waveguide. In general, light incident will be reflected, transmitted or scattered into the various diffraction orders of the grating. Further, at certain angles of incidence, where a diffraction order matches the waveguide propagation condition, light will be coupled into the waveguide.

Here, light will propagate in the guide parallel to the substrate surface, where it will continue to interact with the grating. The light will couple back out of the waveguide via the various diffraction orders and into free-space beams. This outcoupled light will include beams in the same direction as the transmitted and reflected, uncoupled beams.

Attempts to measure the coupling condition are hampered by overlap of the waveguide derived beams and the uncoupled, transmitted or reflected components. This leads to measurements of low contrast.

One approach to this problem is to provide a pair of grating structures separated by an unmodulated region. Light incident on one of the gratings is coupled into the waveguide and is then coupled out by the second grating. The coupled-out light is thus spatially separated from the light reflected or transmitted at the first grating. However, the need for the provision of two gratings is a disadvantage.

In another approach, a single grating structure is employed, the grating structure being a superposition of grating elements having two different periodicities. Light incident on the grating structure at a first angle is coupled into the waveguide by the grating element with a first periodicity. It is then coupled out by the grating element having a second periodicity, at a different angle. The coupled-out light is thus angularly separated from the reflected light. Such a bidiffractive grating is relatively difficult to fabricate.

There haste now been devised methods for monitoring the interaction of molecular species, and devices suitable for use in such methods in which light is coupled into a waveguide by a grating structure, which overcome or substantially mitigate the above-mentioned disadvantages.

SUMMARY OF THE INVENTION

According to a first aspect of the invention, a method for monitoring the interaction of a first molecular species in a sample with a second molecular species comprises providing a sensor device comprising a substrate having a waveguide formed on at least part of the surface thereof, the waveguide having a first major surface which constitutes an interface between the waveguide and the substrate and a second major surface upon which the second molecular species is immobilized, at least a region of the first and/or second major surface being formed with a periodic refractive index modulation;

contacting a sample containing the first molecular species with the second major surface;

irradiating said periodic refractive index modulation with a beam of incident monochromatic light, varying the angle of incidence of said light or the wavelength of said light through a range of angles or wavelengths respectively, said range including an angle or a wavelength, as the case may be, at which a guided mode is excited in said waveguide;

monitoring the intensity of light reflected from said periodic refractive index modulation as a function of the angle of incidence or wavelength of the incident light; and determining the angle of incidence or wavelength at which the intensity of the light reflected from the periodic refractive index modulation is a maximum.

In general, the incident light will be partially reflected from the periodic refractive index modulation, partially transmitted and partially coupled into the waveguide. The method according to the invention is advantageous primarily in that, at a certain angle of incidence, a near-total reflection of the incident light beam can be achieved. The incident light excites a guided mode in the waveguide. This guided mode propagates a certain distance and is then coupled out, back into the substrate and into the superstrate adjacent the waveguide. It is possible by appropriate choice of parameters to achieve almost complete destructive interference of the transmitted components at the coupling angle. This interference is between the zeroth order transmitted beam and the beam radiated from the out-coupled guided wave into the superstrate, ie the material beyond the waveguide (in the direction of the incident light beam).

In such a case there is a correspondingly high intensity of the reflected light at the propagation angle, and this is relatively easily monitored. Such high reflection may be termed "anomalous" or "abnormal" reflection. Interaction of the molecular species immobilized on the waveguide surface with analyte molecules in a sample which is contacted with the waveguide causes a local change in refractive index in the vicinity of the waveguide surface. This in turn changes the angle of incidence or wavelength at which the reflection maximum occurs, providing a sensitive indicator of the chemical interaction taking place at the surface.

The method according to the invention utilises a sensor device with only a single periodic refractive index modulation, and may therefore be easier and/or less expensive to fabricate than devices incorporating multiple gratings or bidiffractive gratings.

By the words "reflected" and "reflection" as used herein we mean the return of the incident light beam from the waveguide through the substrate at an angle equal and opposite to the angle of incidence. Although this is superficially similar to conventional specular reflection, the mechanism of "reflection" in the present case includes diffraction effects from the grating.

The periodic refractive index modulation is preferably a surface relief profile or a grating formed in the surface of the substrate to which the waveguide coating is applied and/or in the surface of the waveguide on which the second molecular species is immobilised. Where the waveguide is formed by a deposition process, the relief profile is preferably formed on the substrate and the waveguide then deposited, e.g. by a chemical vapour deposition process. The periodic refractive index modulation may be formed in one or both major surfaces of the waveguide. Modulation of both surfaces may be created by design or may be a consequence of the fabrication process used. For example, deposition of the waveguide on a relief profile formed in the substrate may result in the surface of the waveguide having a similar corrugation to that of the substrate.

The corrugation may have a variety of forms. For example, it may be sinusoidal, rectangular, triangular (sawtooth) or trapezoidal.

The substrate is conveniently a chip, eg of glass or silica, and, in use, the superstrate is most commonly an aqueous sample. The waveguide is preferably of relatively high refractive index, e.g. a material having a refractive index of, say, 1.80 to 2.50. Suitable materials for the waveguide include hafnium dioxide, silicon nitride, tantalum pentoxide and titanium oxide.

The optimal physical dimensions of the sensor device, grating etc will depend on the wavelength of the incident light. In the following description, the values given for the waveguide thickness, grating depth and period, light beam diameter etc encompass those suitable for commonly-used wavelengths, eg a wavelength of 633 nm.

Typically, the waveguide may have a thickness of the order of 50 nm to 300 nm, more preferably 100 nm to 200 nm. We particularly prefer the thickness of the waveguide to be in the range 140 nm to 180 nm.

The depth of the periodic refractive index modulations (e.g. the corrugations in the surface of the substrate) is preferably less than 50 nm, more preferably less than 25 nm, eg typically 2 nm to 20 nm or 5 nm to 10 nm. The period of the grating is typically 300 nm to 1000 nm, more preferably 600 nm to 1000 nm.

In general, near total reflection of the incident light from the waveguide can be achieved when the radius of the incident beam at the grating exceeds the coupling length of the guided mode in the waveguide, and the dissipative and scattering losses in the waveguide are far less than the radiative losses. As explained above, this "anomalous" or "abnormal" reflection occurs when there is destructive interference of the transmitted light at the angle of propagation within the waveguide.

Thus, the invention provides a method of monitoring the interaction of the first and second molecular species, which method utilizes a device of the type generally described above and comprises monitoring the angle of incidence (or wavelength) at which the abnormal reflection maximum condition occurs.

Although, in theory, the reflection of the incident beam may be nearly total, in practice instrumental and other factors usually mean that the intensity of the reflected beam is somewhat less than this. Nonetheless, the reflected intensity is still sufficiently great to provide a clear maximum.

In general, satisfactory results can be obtained when the maximum reflected intensity (eg occurring when the anomalous reflection conditions are met) is greater than about 20% of the intensity of the beam incident upon the substrate, more preferably greater than 30% or 40%.

The position of the reflection maximum may be determined only before and after the first and second molecular species are brought into contact, eg to provide a qualitative and/or quantitative indication of the presence of the first molecular species in the sample. Alternatively, the position of the reflection maximum may be monitored periodically or continuously in real time, eg to provide information on the progress and kinetics of the interaction.

Where the device is irradiated from below the substrate, it is strongly preferred that reflection from the underside of the substrate be minimal. To achieve this, the beam of incident light is preferably TM-polarized and the angle of incidence of the light beam on the substrate is preferably close to the Brewster angle, ie the angle $\theta_B = \tan^{-1}(n_s)$ where $n_s$ is the refractive index of the substrate. Alternatively, the underside of the substrate may carry an anti-reflection coating.

The beam of incident light preferably has a diameter of less than 10 mm, eg 1 mm to 8 mm, more preferably less than 6 mm, eg 2 mm to 5 mm.

It is also preferred that the point at which the beam of incident light is incident upon the periodic refractive index modulation be offset from the centre of that modulation. The length of the grating is preferably less than 20 mm, more preferably less than 10 mm, eg about 7 mm. In such a case, the incident light beam is preferably offset from the centre of the grating by less than 1 mm, eg 0.2 to 0.6 mm. The effect of this offset is to minimise the grating area required to achieve a given sensitivity. Since a major contributor to the cost of fabrication is the size of the grating used, any measure which reduces the size of grating required (without reducing the device sensitivity) is beneficial.

As mentioned above, the optimal dimensions for the grating etc are wavelength-dependent. Relating the various parameters to the wavelength $\lambda$, the following ranges are typical:

waveguide thickness: $\lambda/12$ to $\lambda/2$ grating depth: $\lambda/300$ to $\lambda/12$, more preferably $\lambda/300$ to $\lambda/30$ grating period: $\lambda/2$ to $2\lambda$, more preferably $\lambda$ to $1.5\lambda$.

The background reflection, ie the intensity of the reflected light at angles/wavelengths away from that at which a guided mode is coupled into the waveguide, may be reduced by choosing a waveguide thickness which minimises Fresnel reflection.

The means for generating the incident beam of monochromatic light may be any conventional source of monochromatic radiation, most preferably a laser light source. By "light" is meant in this context not only visible light, but also wavelengths above and below that range, e.g. in the infra-red and ultra-violet.

Appropriate collimating and/or polarising optical components may be interposed between the light source and the sensor, as required.

The beam of incident light may be scanned sequentially through a range of angles of incidence. This may be achieved by optical manipulation of the light beam, or by physical movement of the light source.

Where the wavelength of the incident light is varied, this may be achieved by the use of a tunable light source such as a tunable laser.

The means for monitoring the intensity of the radiation reflected from the device may be a conventional detector, e.g. a photoelectric detector such as a charge coupled device (CCD) or an array of such devices. It may be necessary for the detector to be moved in synchronism with variation in the angle of incidence.

The second molecular species is immobilised on the surface of the waveguide. Suitable methods for such immobilization will be familiar to those skilled in the art. The second molecular species may be immobilized directly on the waveguide surface, or may be indirectly linked to the surface. The second molecular species may be linked to the surface through covalent bonds to intermediate chemical species or by physical interaction with other immobilised species, or may be chemically or physically bound to a coating layer, eg a hydrogel matrix or other polymeric coating, applied to the waveguide surface.

It may be possible to use the apparatus and method of the invention in a manner which provides internal compensation for systematic errors such as temperature fluctuations or variations in the position of the incident beam etc. To this end, a dual-mode waveguide may be used or simultaneous irradiation at two different wavelengths, giving rise to a pair of resonances (ie a pair of angles/wavelengths at which coupling occurs). The sensitivities of the two resonances (ie the dependence of the positions of the resonances on the interaction of first and second molecular species) will generally be different.

According to a second aspect of the present invention, apparatus for monitoring the interaction of a first molecular species with a second molecular species comprises a sensor device comprising a substrate having a waveguide formed on at least part of the surface thereof, the waveguide having a first major surface which constitutes an interface between the waveguide and the substrate and a second major surface upon which the second molecular species is immobilized, at least a region of the first and/or second major surface being formed with a periodic refractive index modulation;

means for irradiating said periodic refractive index modulation with a beam of incident monochromatic light, means for varying the angle of incidence of said light or the wavelength of said light through a range of angles or wavelengths respectively, said range including an angle or a wavelength, as the case may be, at which a guided mode is excited in said waveguide; and means for monitoring the intensity of light reflected from said periodic refractive index modulation as a function of the angle of incidence or wavelength of the incident light;

means for determining the angle of incidence or wavelength at which the intensity of the reflected light is a maximum.

Preferably, the means for irradiating the periodic refractive index modulation includes means for irradiating the substrate at an angle or range of angles of incidence which is close to, or includes, the Brewster angle.

Preferably, the apparatus further comprises means for polarizing the incident light beam such that the light incident upon the sensor device is TM-polarized.

Preferably, the dimensions and form of the waveguide and the grating are described above.

BRIEF DESCRIPTION OF THE DRAWINGS

The invention will now be described in greater detail, by way of illustration only, with reference to the accompanying Figures, in which.

DETAILED DESCRIPTION OF THE INVENTION

Figure 1:
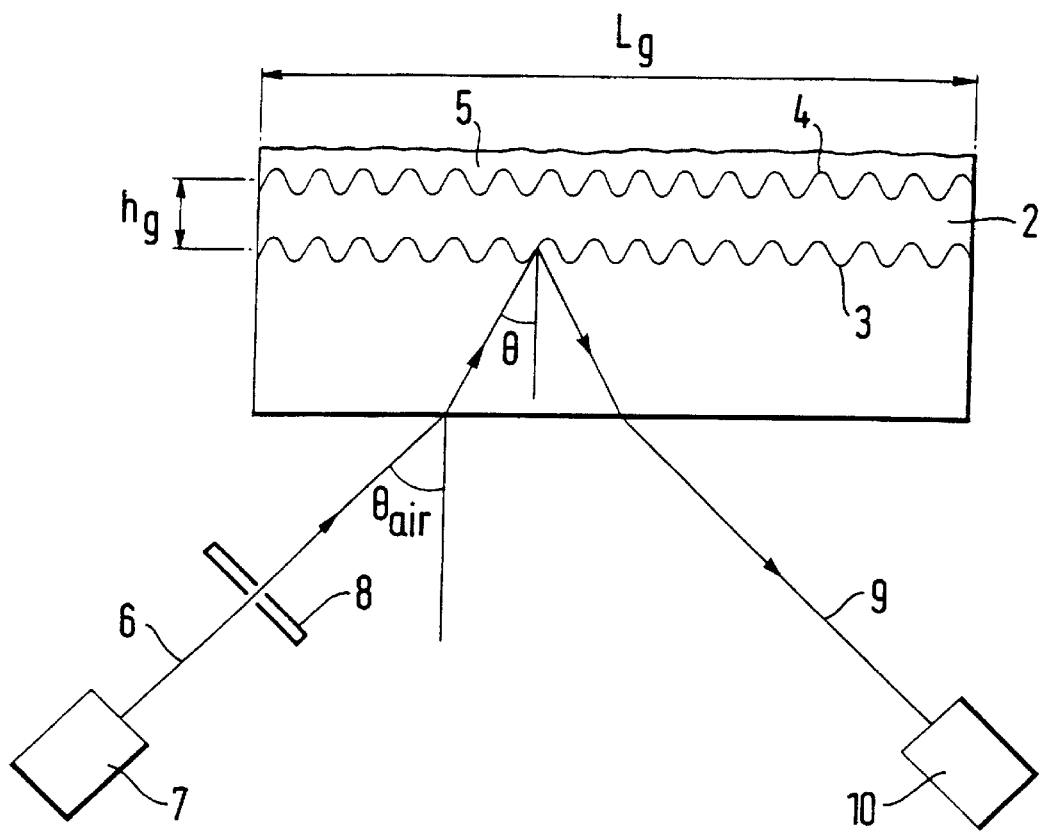
FIG. 1 is a schematic view (not to scale) of a biosensor device according to the invention.

Referring first to FIG. 1, a biosensor device comprises a substrate in the form of a chip 1 (eg of glass or silica) approximately 7 mm square and 2 mm in thickness. The chip 1 has a refractive index of 1.46. Coated on the upper surface of the chip 1 is a waveguide 2.

The interface between the chip 1 and the waveguide 2 is formed with a periodic relief profile or grating 3 (the grating 3 is shown as being sinusoidal though in practice a generally rectangular profile is produced by the method of fabrication described below). The waveguide 2 is formed by deposition on the chip 1 and a corresponding relief profile 4 may thus be formed also on the upper surface of the waveguide 2. A layer 5 of biomolecules, eg antibodies, is immobilized on the upper surface of the waveguide 2 in a known manner.

A beam 6 of monochromatic light ($\lambda$=633 nm) is produced by a laser light source 7. The beam 6 passes through a polarizer 8 and is incident on the underside of the chip 1 at an angle $\theta_{air}$. The angle of incidence $\theta_{air}$ of the light beam 6 on the base of the chip 1 may be varied through a range of angles. Such variation may be brought about by mechanical movement of the light source 7 and/or optical deviation of the incident beam 6. The intensity of a reflected beam 9 of light reflected from the device is measured by a suitable detector 10.

The process by which the structure and operating parameters of the device of FIG. 1 are optimised will now be described. The process has three stages:

a) Selection of angle of incidence $\theta_{air}$

Fresnel reflection from the underside of the chip 1 is minimized by arranging the polarizer 8 such that the incident light beam 6 is TM-polarized. Advantage is then taken of the Brewster effect by choosing the angle of incidence $\theta_{air}$ air according to $$\theta_{air} = \tan^{-1} n_s$$

where $n_s$=refractive index of the chip 1.

This gives an angle of incidence $\theta$ on the grating 3 which is $$\theta = \sin^{-1}\left[\frac{\sin\theta_{air}}{n_s}\right]$$

For a glass chip 1, with $n_s$=1.51, $\theta_{air}$=56.49° and $\theta$=33.51°. If silica were used as the substrate material, the corresponding figures would be $n_s$=1.46, $\theta_{air}$=55.59° and $\theta$=34.41°.

b) Determination of the waveguide parameters

Figure 2:
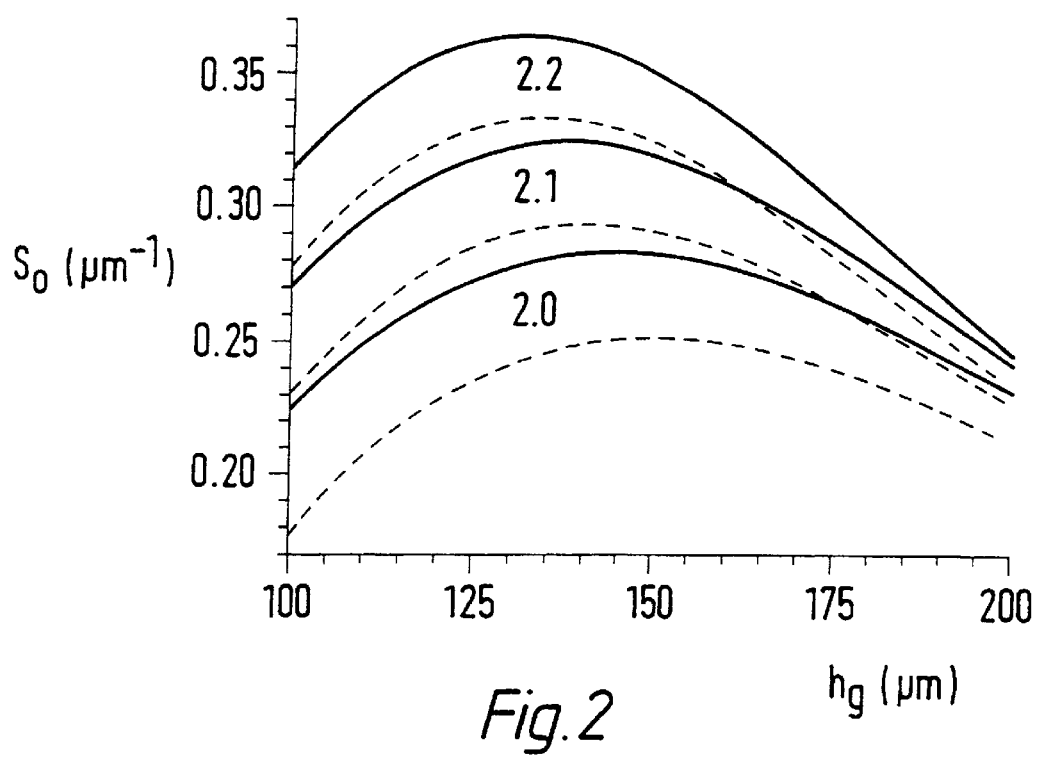
FIG. 2 shows the mode sensitivity $S_0$, as a function of waveguide thickness, for a waveguide formed on a glass (broken lines) or silica (solid lines) substrate.

The optimum waveguide thickness $h_g$ for a given waveguide refractive index is now determined. First, the waveguide thickness is determined by maximizing the $TM_0$ mode sensitivity $S_0$. An example of the dependence of the sensor sensitivity on the waveguide thickness, and of the optimum value $h_{gS}$ corresponding to the maximum sensitivity is shown in FIG. 2. This shows the sensitivity $S_0$ as a function of waveguide thickness $h_g$ for a silica substrate (solid curves) and a glass substrate (broken curves) at each of three values of waveguide refractive index $n_g$ (2.0, 2.1 and 2.2). As can be seen, the waveguide thickness $h_g$ which gives greatest sensitivity (which we designate $h_{gS}$) varies between about 130 nm and 150 nm.

Secondly, since the waveguide 2 has two boundaries, it is possible to use the effect of interference of reflections from these two interfaces to substantially reduce the overall Fresnel reflection for an incidence angle close to but outside the resonance.

Figure 3:
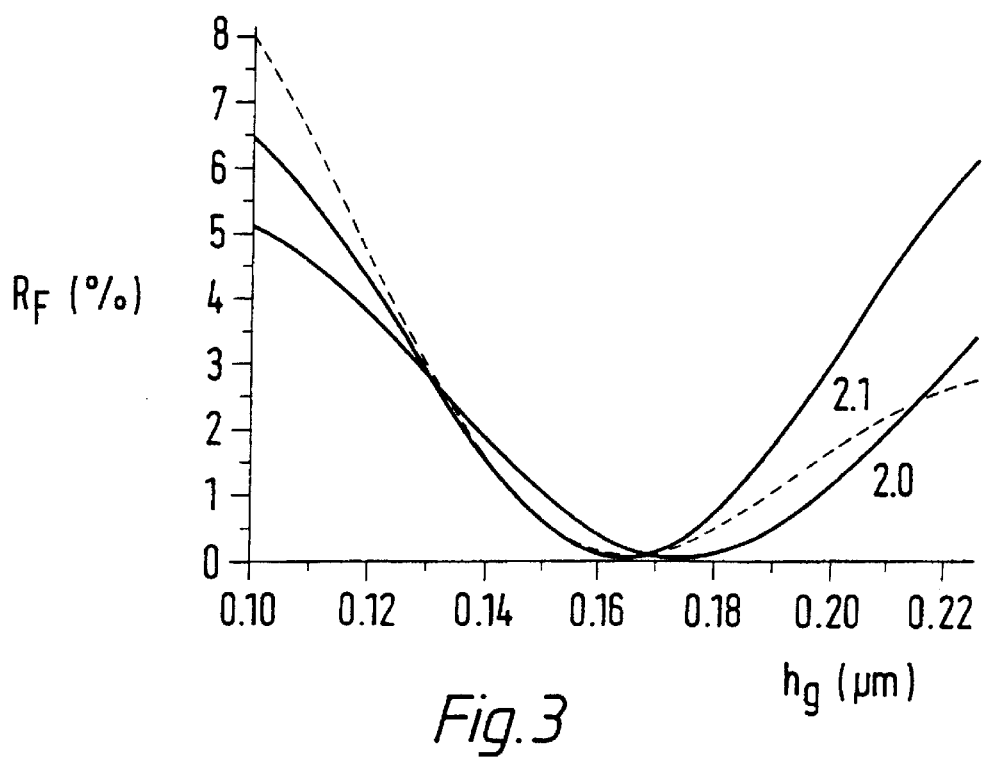
FIG. 3 shows the Fresnel reflection coefficient $R_F$ as a function of waveguide thickness, for a waveguide formed on a glass (broken lines) or silica (solid lines) substrate.

Typical data for Fresnel reflection coefficient $R_F$ versus waveguide thickness (for a planar waveguide formed on a silica or glass substrate—solid and broken lines respectively) is presented in FIG. 3. In the case of a silica substrate, data is shown for two values of waveguide refractive index $n_g$=2.0 and 2.1. The waveguide thickness corresponding to the minimum reflection is denoted $h_{gR}$. The optimum waveguide thickness is a compromise between the condition of maximum sensitivity $h_g$=$h_{gS}$, and condition $h_g$=$h_{gR}$ for minimum Fresnel reflection. Fortunately, these two conditions are close to each other. The waveguide thickness $h_g$ is therefore chosen in the interval between $h_{gS}$ and $h_{gR}$. Preferably, $h_g$ is chosen closer to $h_{gR}$ to get a high quality reflection peak while losing no more than 10% sensitivity. For example, $n_g$=2.0 leads to an optimum waveguide layer thickness $h_g$=0.17 µm; $n_g$=2.1 leads to an optimum waveguide layer thickness $h_g$=0.165 µm. The reflection coefficient $R_F$ is ~0.1% in both cases.

c) Determination of the grating parameters

Now, for a given waveguide structure, it is possible to calculate the effective refractive index $n_{e0}$ of the fundamental mode and then the desired period $\Lambda$ of the waveguide corrugation:

$$\Lambda = \frac{\lambda}{n_{e0} - n_S \sin\theta}$$

Figure 4:
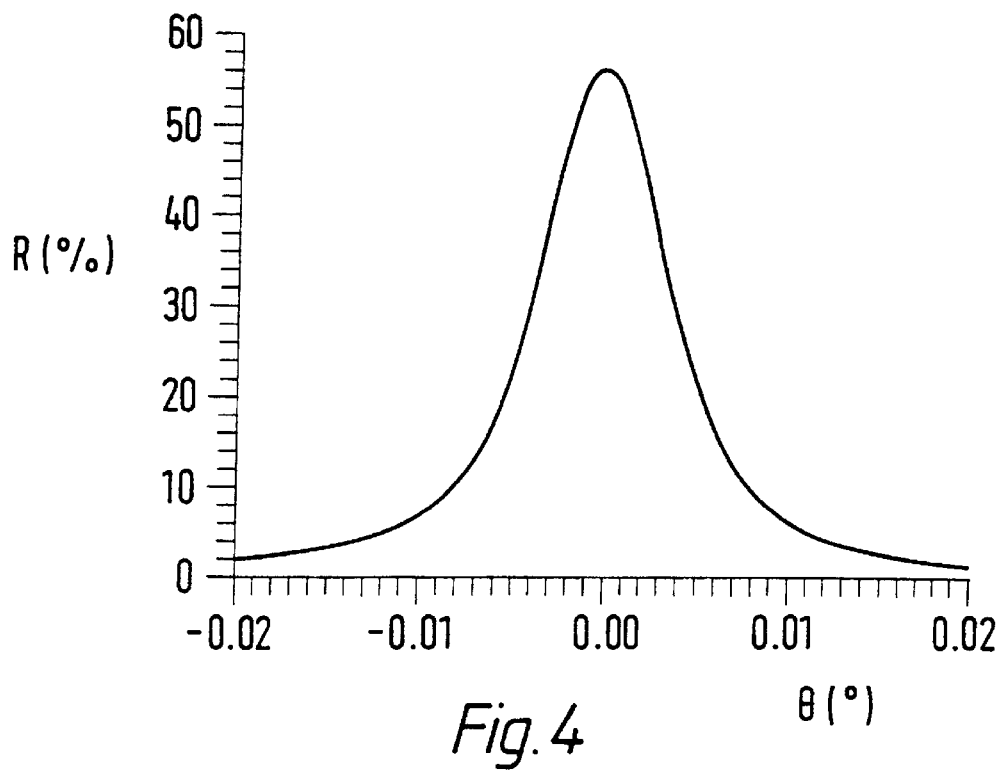
FIG. 4 represents the power of radiation reflected from the biosensor device of FIG. 1 as a function of the deviation of the angle of incidence from an angle at which the reflection is a maximum.

In order to obtain high reflection it is necessary that the following condition be satisfied:

$$\frac{\alpha w}{\cos\theta} \gg 1$$

where $w$ is the radius of the incident Gaussian beam 6 (ie half the full width of the beam at half-height), and $\alpha$ is the total loss coefficient in the waveguide. FIG. 4 shows an example of the dependence of the normalized reflected power R on the angle of incidence (shown as a deviation from the angle giving maximum reflection). The peak quality may be expressed in terms of a parameter $F_{opt}$=$R_{max}$/$\Delta\theta$ where $R_{max}$ is the amplitude of the peak and $\Delta\theta$ is its angular width at half-height. A "figure of merit" may also be obtained by multiplying $F_{opt}$ by the mode sensitivity $S_0$.

It is found that for a grating of length $L_g$ the total losses $\alpha$, beam radius $w$, and beam centre position $\Delta z$ on the grating area should satisfy the following approximate conditions:

$$\alpha \approx \frac{4.06}{L_g} \quad \frac{w}{\cos\theta} \approx 0.44 L_g \quad \Delta z \approx 0.44 L_g$$

For a grating length $L_g$=7 mm, the following figures are obtained:

| | |
|---|---|
| Full loss coefficient | $\alpha$ = 5.8 cm$^{-1}$ |
| Radius of Gaussian beam in the grating plane | $\frac{w}{\cos\theta}$ = 3.1 mm |
| Radius of Gaussian beam in the substrate | $w$ = 2.5 mm |
| Distance of beam centre to grating edge | $\Delta z$ = 3.1 mm |

The value of the loss coefficient in the waveguide determines the necessary groove depth. Considering, as an approximation, a sinusoidal groove profile and a single corrugated boundary, the groove depth can be calculated using known analytical formulae [(see, for example, Y. Yamamoto et al, IEEE J. Quant. Electron., QE-14, 620–625 (1978)].

Figure 5:
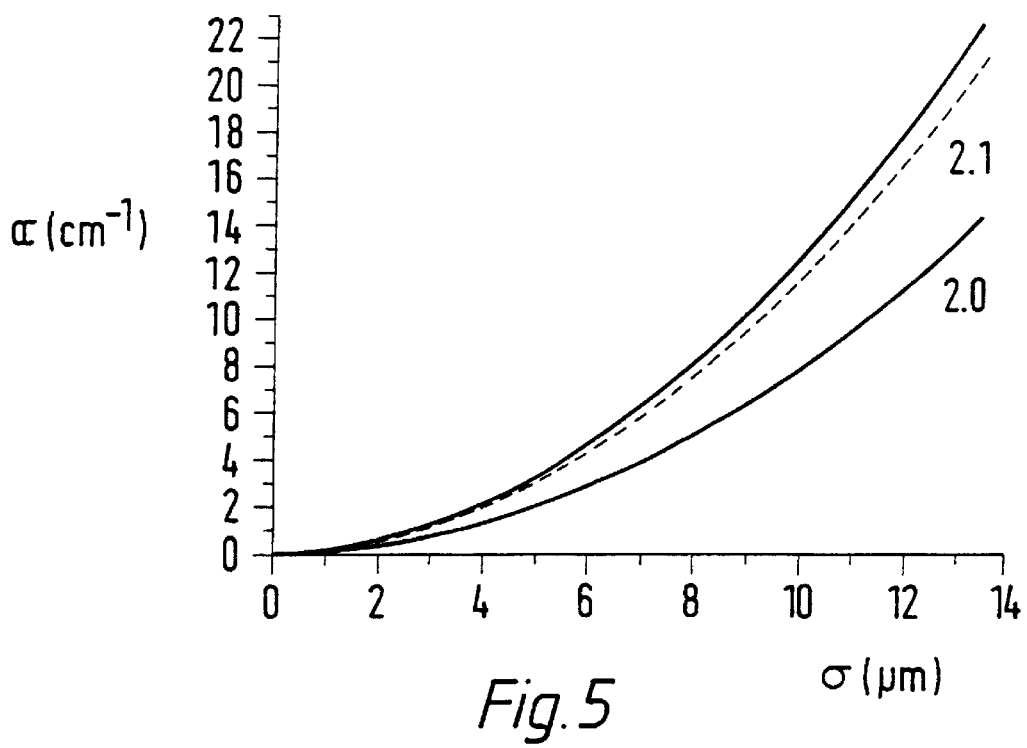
FIG. 5 shows the radiative loss coefficient $\alpha$ as a function of grating groove depth for a biosensor device similar to that shown in FIG. 1 (with a rectangular grating profile)

FIG. 5 shows the radiative loss coefficient $\alpha$ as a function of groove depth $\sigma$ for a silica substrate (solid lines) at two values of waveguide refractive index $n_g$=2.0 and 2.1, and for a glass substrate (broken line) at $n_g$=2.1. In each case, the groove depth $\sigma$ corresponding to the previously determined value of $\alpha$=5.8 cm$^{-1}$ can be read off.

In summary, for a given choice of substrate and waveguide materials, and a given wavelength, the optimum angle of incidence is chosen to minimise reflection from the underside of the substrate, the waveguide thickness is chosen as a compromise between maximum sensitivity and minimum Fresnel reflection, and finally the grating parameters (period, groove depth) are optimised.

Table I summarizes the optimum parameters derived as described above for three different combinations of waveguide and substrate materials, the wavelength of the light used being 633 nm in all cases and the grating length 7 mm.

TABLE I

| Parameter | Structure 1 | Structure 2 | Structure 3 |
|---|---|---|---|
| *Waveguide parameters* | | | |
| Substrate refractive index | 1.46 | 1.46 | 1.51 |
| Waveguide refractive index | 2.0 | 2.1 | 2.1 |
| Waveguide thickness $h_g$ (nm) | 160 | 165 | 164 |
| Effective refractive index (without grating) | 1.61308 | 1.68258 | 1.69759 |
| *Grating parameters* | | | |
| Grating period $\Lambda$ ($\mu$m) | 0.8 | 0.74 | 0.73 |
| Groove depth $\sigma$ (nm) | 8.6 | 6.8 | 7.2 |
| Loss coefficient $\alpha$ (cm$^{-1}$) | 5.80 | 5.69 | 6.02 |
| Effective refractive index (with grating) | 1.61337 | 1.68291 | 1.69789 |
| *Geometrical parameters* | | | |
| Incidence angle $\theta_{air}$ in the air (degrees) | 55.32 | 55.87 | 56.21 |
| Incidence angle $\theta$ in the substrate (degrees) | 34.28 | 34.54 | 33.39 |
| Incident beam radius $w_{air}$ in the air (mm) | 1.77 | 1.77 | 1.66 |
| Incidence beam radius $w$ in the substrate (mm) | 2.56 | 2.61 | 2.5 |
| Beam centre position $\Delta z$ at the grating (mm) | 3.10 | 3.16 | 2.99 |
| *Biosensor merit* | | | |
| Mode sensitivity $S_0$ ($\mu$m$^{-1}$) | 0.279 | 0.304 | 0.281 |
| Peak width $\Delta\theta$ (degrees) | 0.0084 | 0.0083 | 0.0082 |
| Maximum reflection $R_{max}$ (%) | 51.7 | 53.5 | 54.2 |
| Reflection out of resonance $R_F$ | 0.4 | 0.05 | 0.09 |
| Reflection from the substrate (%) | 0.0007 | 0.0008 | 0.0009 |
| Peak quality $F_{opt} = \dfrac{R_{max}}{\Delta\theta}$ (%/degrees) | 6155 | 6446 | 6610 |
| Figure of merit $S_0 F_{opt}$ (%/degrees/$\mu$m) | 1717 | 1960 | 1717 |

It can be seen from FIG. 4 that there is one particular angle at which greatly increased reflection occurs with very low background. This angle is sensitive inter alia to the refractive index in the immediate vicinity of the upper surface of the waveguide 2. Changes in this refractive index, e.g. as a result of binding of biomolecules in a sample contacted with the surface of the waveguide 2 with the immobilized biomolecules on that surface, cause shifts in the angular position of the reflection maximum. Such shifts indicate the extent of interaction between the analyte biomolecules in the sample and the immobilized biomolecules.

Thus, the sensor device according to the invention may be used to investigate such interactions. For example, the angle of incidence $\theta$ of the light beam 6 may be scanned through a range of angles encompassing the angle at which the reflection maximum occurs and the position of that maximum is determined. The sample to be investigated is then contacted with the surface of the waveguide 2 and the process repeated. Continuous real-time measurements may be made to follow the interaction process.

Most conveniently, the measured data (reflected intensity as a function of angle of incidence and time) are digitised and stored in a computer unit connected to the sensor device.

It can be seen from Table I that the optimum groove depth is very small. The fabrication of such a grating structure presents certain difficulties but one method by which it can be achieved is as follows (see FIG. 6).

Figure 6A:
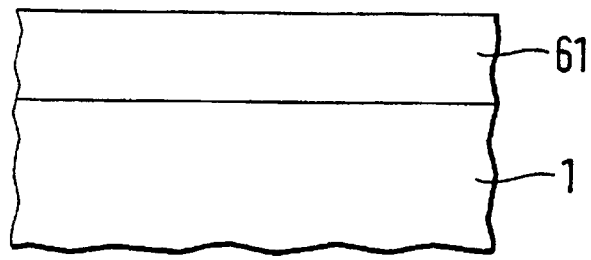
FIG. 6 illustrates stages in the manufacture of a sensor device as shown in FIG. 1.
Figure 6B:
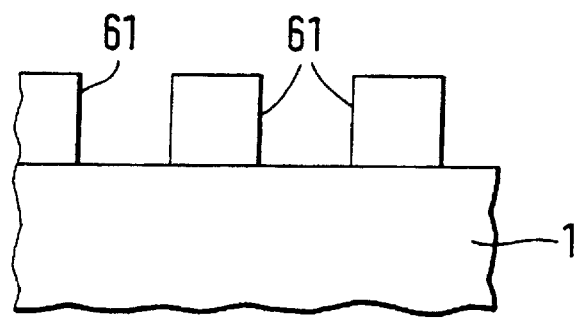
Figure 6C:
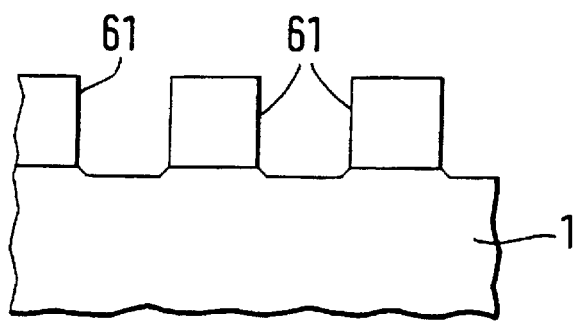
Figure 6D:
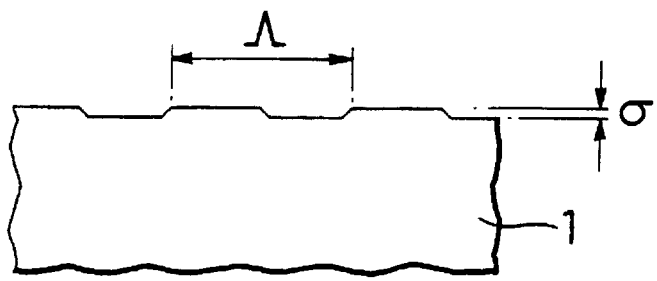
Figure 6E:
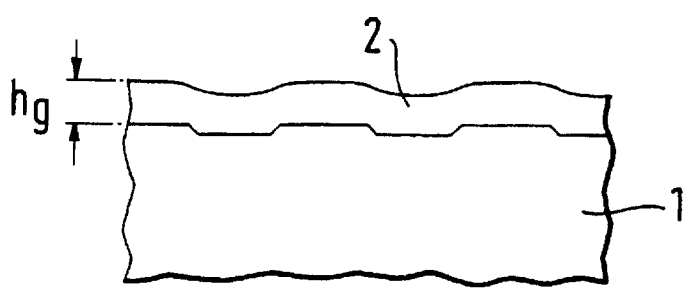

First, a layer of photoresist 61 is deposited onto the surface of the substrate 1 (FIG. 6a). The photoresist has a thickness of approximately 700 nm. The grating pattern is then exposed into the photoresist 61, eg through a mash or by a direct holographic method using crossed laser beams, and developed to reveal the grating pattern (FIG. 6b). The surface of the substrate 1 is then etched through the photoresist, eg using reactive ion-etching, ion-beam etching or wet etching, the exposed surface regions of the substrate 1 being removed (see FIG. 6c) to the desired depth (typically 5–10 nm). The remaining photoresist is then removed (FIG. 6d) and the waveguide 2 then deposited (FIG. 6e), eg by a chemical vapour deposition process.

What is claimed is:

1. A method for monitoring the interaction of a first molecular species in a sample with a second molecular species, said method comprising:

providing a sensor device comprising a substrate having a waveguide formed on at least part of the surface thereof, the waveguide having a first major surface which constitutes an interface between the waveguide and the substrate and a second major surface upon which the second molecular species is immobilized, wherein one or both of at least a region of the first major surface and at least a region of the second major surface is formed with a refractive index modulation having a single period, and where both first and second major surfaces are formed with such a refractive index modulation, the periods of both of said refractive index modulations being the same;

contacting a sample containing the first molecular species with the second major surface so that interaction between the first molecular species and the second molecular species can take place;

irradiating said refractive index modulation with an incident beam of monochromatic incident light having a wavelength and the incident beam having a radius, varying an angle of incidence of said light or the wavelength of said light through a range of angles or wavelengths respectively, said range including an angle or a wavelength, as the case may be, at which a guided mode is excited in said waveguide;

monitoring intensity of light reflected from said refractive index modulation as a function of the angle of incidence or wavelength of the incident light; and determining that angle of incidence or wavelength at which light reflected from the refractive index modulation has a maximum intensity, such that at that angle of incidence or wavelength at which light reflected from the refractive index modulation has a maximum intensity there is destructive interference of transmitted components of incident light, and the radius of the incident beam at the refractive index modulation exceeds a coupling length of the guided mode in the waveguide, and wherein that angle of incidence or wavelength at which light reflected from the refractive index modulation has a maximum intensity is dependent upon interaction of the first molecular species with the second molecular species.

2. A method as claimed in claim 1, wherein light reflected from the refractive index modulation has a maximum intensity greater than 20% of that of light incident on the substrate.

3. A method as claimed in claim 2, wherein light reflected from the refractive index modulation has a maximum intensity greater than 30% of that of light incident on the substrate.

4. A method as claimed in claim 1, wherein the refractive index modulation is a surface relief profile or a grating formed in the surface of the substrate to which the waveguide is applied and/or in the surface of the waveguide on which the second molecular species is immobilized.

5. A method as claimed in claim 4, wherein the surface relief profile is sinusoidal, rectangular, triangular or trapezoidal.

6. A method as claimed in claim 1, wherein the substrate is a chip of glass or silica.

7. A method as claimed in claim 1, wherein the waveguide has a refractive index of between 1.80 and 2.50.

8. A method as claimed in claim 1, wherein the waveguide is of a material selected from the group consisting of hafnium dioxide, silicon nitride, tantalum pentoxide and titanium oxide.

9. A method as claimed in claim 1, wherein the waveguide has a thickness of 100 nm to 200 nm.

10. A method as claimed in claim 1, wherein the waveguide has a thickness of 140 nm to 180 nm.

11. A method as claimed in claim 1, wherein the refractive index modulation has a depth of less than 50 nm.

12. A method as claimed in claim 1, wherein the refractive index modulation has a depth of between 2 nm and 20 nm.

13. A method as claimed in claim 1, wherein the period of the refractive index modulation is between 600 nm and 1000 nm.

14. A method as claimed in claim 1, wherein the incident beam is TM-polarized.

15. A method as claimed in claim 1, wherein the angle of incidence of the incident beam is, or is close to, the Brewster angle, or the range of angles includes the Brewster angle.

16. A method as claimed in claim 1, wherein the incident beam has a diameter of less than 10 mm.

17. A method as claimed in claim 16, wherein the incident beam has a diameter of 1 to 8 mm.

18. A method as claimed in claim 1, wherein a point at which the incident beam is incident upon the refractive index modulation is offset from a centre of that modulation.

19. A method as claimed in claim 18, wherein the refractive index modulation has a length of less than 10 mm and the incident beam is offset from the centre of the modulation by less than 1 mm.

20. A method as claimed in claim 1, wherein the incident beam has a fixed wavelength $\lambda$, the waveguide has a thickness in the range $\lambda/12$ to $\lambda/2$, the refractive index modulation has a depth in the range $\lambda/300$ to $\lambda/12$, and the period of the modulation is in the range $\lambda/2$ to $2\lambda$.

21. A method as claimed in claim 1, wherein that angle of incidence or wavelength at which the intensity of light reflected from the refractive index modulation is a maximum is determined before and after the first and second molecular species are brought into contact.

22. A method as claimed in claim 1, wherein that angle of incidence or wavelength at which the intensity of light reflected from the refractive index modulation is a maximum is determined periodically or continuously in real time after the first and second molecular species are brought into contact.

23. A method of fabricating a sensor device for use in the method of claim 1, which comprises
   a) coating a substrate with a masking material;
   b) removing parts of the masking material to reveal exposed substrate regions;
   c) etching the surface of the substrate in the exposed substrate regions;
   d) removing all remaining masking material; and
   e) depositing a waveguide on the surface of the substrate.

24. Apparatus for monitoring the interaction of a first molecular species with a second molecular species, said apparatus comprising a sensor device comprising a substrate having a waveguide formed on at least part of the surface thereof, the waveguide having a first major surface which constitutes an interface between the waveguide and the substrate and a second major surface upon which the second molecular species is immobilized, wherein one or both of at least a region of the first major surface and at least of a region of the second major surface is formed with a refractive index modulation having a single period, and where both first and second major surfaces are formed with such a refractive index modulation, the periods of both of said refractive index modulations being the same;

means for irradiating said refractive index modulation with an incident beam of monochromatic incident light having a wavelength and the incident beam having a radius, means for varying an angle of incidence of said light or the wavelength of said light through a range of angles or wavelengths respectively, said range including an angle or a wavelength, as the case may be, at which a guided mode is excited in said waveguide; and means for monitoring intensity of light reflected from said refractive index modulation as a function of the angle of incidence or wavelength of the incident light;

means for determining that angle of incidence or wavelength at which light reflected from the refractive index modulation has a maximum intensity, such that at that angle of incidence or wavelength at which light reflected from the refractive index modulation has a maximum intensity there is destructive interference of transmitted components of incident light, and the radius of the incident beam at the refractive index modulation exceeds a coupling length of the guided mode in the waveguide, and wherein that angle of incidence or wavelength at which light reflected from the refractive index modulation has a maximum intensity is dependent upon interaction of the first molecular species with the second molecular species.

25. Apparatus as claimed in claim 24, wherein light reflected from the refractive index modulation has a maximum intensity greater than 20% of that of light incident on the substrate.

26. Apparatus as claimed in claim 25, wherein light reflected from the refractive index modulation has a maximum intensity greater than 30% of that of light incident on the substrate.

27. Apparatus as claimed in claim 24, wherein the refractive index modulation is a surface relief profile or a grating formed in the surface of the substrate to which the waveguide is applied and/or in the surface of the waveguide on which the second molecular species is immobilized.

28. Apparatus as claimed in claim 27, wherein the surface relief profile is sinusoidal, rectangular, triangular or trapezoidal.

29. Apparatus as claimed in claim 24, wherein the substrate is a chip of glass or silica.

30. Apparatus as claimed in claim 24, wherein the waveguide has a refractive index of between 1.80 and 2.50.

31. Apparatus as claimed in claim 24, wherein the waveguide is of a material selected from the group consisting of hafnium dioxide, silicon nitride, tantalum pentoxide and titanium oxide.

32. Apparatus as claimed in claim 24, wherein the waveguide has a thickness of 100 nm to 200 nm.

33. Apparatus as claimed in claim 24, wherein the waveguide has a thickness of 140 nm to 180 nm.

34. Apparatus as claimed in claim 24, wherein the refractive index modulation has a depth less than 50 nm.

35. Apparatus as claimed in claim 24, wherein the refractive index modulation has a depth between 2 nm and 20 nm.

36. Apparatus as claimed in claim 24, wherein the period of the refractive index modulation is between 600 nm and 1000 nm.

37. Apparatus as claimed in claim 24, wherein the incident beam has a diameter of less than 10 mm.

38. Apparatus as claimed in claim 24, wherein a point at which the incident beam is incident upon the refractive index modulation is offset from a centre of that modulation.

39. Apparatus as claimed in claim 38, wherein the refractive index modulation has a length of less than 10 mm and the incident beam is offset from the centre of the modulation by less than 1 mm.

40. Apparatus as claimed in claim 24, wherein the incident beam has a fixed wavelength $\lambda$, the waveguide has a thickness in the range $\lambda/12$ to $\lambda/2$, the refractive index modulation has a depth in the range $\lambda/300$ to $\lambda/12$, and the period of the modulation is in the range $\lambda/2$ to $2\lambda$.

41. Apparatus as claimed in claim 24, further comprising means for polarizing the incident beam such that light incident upon the sensor device is TM-polarized.

42. Apparatus as claimed in claim 41, wherein the angle of incidence of the incident beam is, or is close to, the Brewster angle, or the range of angles includes the Brewster angle.

43. Apparatus as claimed in claim 24, wherein the incident beam has a diameter of 1 to 8 mm.

* * * * *